(12) United States Patent
Cobb et al.

(10) Patent No.: US 11,921,102 B2
(45) Date of Patent: *Mar. 5, 2024

(54) COMPACT OPTICAL IMAGING SYSTEM FOR CELL CULTURE MONITORING

(71) Applicant: CORNING INCORPORATED, Corning, NY (US)

(72) Inventors: Joshua Monroe Cobb, Victor, NY (US); Mark Christian Sanson, Macedon, NY (US)

(73) Assignee: CORNING INCORPORATED, Corning, NY (US)

( * ) Notice: Subject to any disclaimer, the term of this patent is extended or adjusted under 35 U.S.C. 154(b) by 347 days.

This patent is subject to a terminal disclaimer.

(21) Appl. No.: 16/690,583

(22) Filed: Nov. 21, 2019

(65) Prior Publication Data

US 2020/0173977 A1 Jun. 4, 2020

Related U.S. Application Data

(60) Provisional application No. 62/773,899, filed on Nov. 30, 2018.

(51) Int. Cl.
*C12M 3/00* (2006.01)
*C12M 1/00* (2006.01)
(Continued)

(52) U.S. Cl.
CPC ......... *G01N 33/4833* (2013.01); *C12M 23/12* (2013.01); *C12M 41/46* (2013.01);
(Continued)

(58) Field of Classification Search
CPC ...... C12M 41/06; C12M 31/08; C12M 41/46; G01N 33/4833
See application file for complete search history.

(56) References Cited

U.S. PATENT DOCUMENTS 5,470,746 A * 11/1995 Kim ................. C12M 41/34
435/287.1
5,715,933 A 2/1998 Monahan
(Continued)

FOREIGN PATENT DOCUMENTS

CN 101477046 A 7/2009
CN 105907634 A 8/2016
(Continued)

OTHER PUBLICATIONS

International Search Report and Written Opinion of the International Searching Authority; PCT/US2019/062137; dated Jun. 25, 2020; 18 Pages; European Patent Office.
(Continued)

*Primary Examiner* — Nathan A Bowers
(74) *Attorney, Agent, or Firm* — Chandra J. Duncan (57) ABSTRACT

An optical imaging system for cell culture monitoring is provided. The system includes an illumination segment having an illumination source and a collimating lens positioned between a first surface of a cell culture vessel and the illumination source. The illumination source and the collimating lens are arranged to transmit light through the first surface at an angle oblique to the first surface of the cell culture vessel. The system also includes a detection segment having a detector and a lens positioned between the first surface of the cell culture vessel and the detector. The lens focuses light to the detector through an aperture stop, and the detector receives light that exits the first surface of the cell culture vessel at an angle oblique to the first surface.

21 Claims, 6 Drawing Sheets

(51) Int. Cl.
  *C12M 1/32* (2006.01)
  *C12M 1/34* (2006.01)
  *G01N 21/55* (2014.01)
  *G01N 33/483* (2006.01)
  *G01N 33/50* (2006.01)
  *G02B 21/36* (2006.01)
  *G02B 21/00* (2006.01)
  *G02B 21/04* (2006.01)

(52) U.S. Cl.
  CPC ......... *G01N 21/55* (2013.01); *G01N 33/5005* (2013.01); *G02B 21/361* (2013.01); *G02B 21/002* (2013.01); *G02B 21/04* (2013.01); *G02B 21/36* (2013.01)

(56) References Cited

U.S. PATENT DOCUMENTS

| | | | |
|---|---|---|---|
| 5,858,769 A * | 1/1999 | DiGuiseppi | C12M 23/38 435/287.3 |
| 5,926,311 A | 7/1999 | Cobb et al. | |
| 6,795,239 B2 | 9/2004 | Tandler et al. | |
| 7,796,328 B2 | 9/2010 | Wolleschensky | |
| 10,501,718 B2 | 12/2019 | Matsushita et al. | |
| 2003/0231537 A1 | 12/2003 | Stark | |
| 2005/0219526 A1 * | 10/2005 | Peng | G01N 21/274 356/338 |
| 2006/0166305 A1 | 7/2006 | Jiang et al. | |
| 2008/0068710 A1 | 3/2008 | Wolleschensky | |
| 2008/0082468 A1 | 4/2008 | Long et al. | |
| 2008/0266545 A1 * | 10/2008 | Hansen | G01N 21/6428 356/39 |
| 2010/0035337 A1 | 2/2010 | Bahnemann et al. | |
| 2013/0038727 A1 | 2/2013 | Clark | |
| 2013/0176897 A1 | 7/2013 | Wang et al. | |
| 2015/0087240 A1 | 3/2015 | Loewke et al. | |
| 2015/0329813 A1 * | 11/2015 | Martin | C12M 25/02 435/294.1 |
| 2016/0299069 A1 | 10/2016 | Tao et al. | |
| 2017/0044481 A1 | 2/2017 | Kawano et al. | |
| 2017/0145370 A1 * | 5/2017 | Kato | C12M 41/36 |
| 2018/0045944 A1 | 2/2018 | Suzuki | |
| 2018/0252648 A1 | 9/2018 | Dohi | |
| 2018/0291328 A1 * | 10/2018 | Sasaki | C12M 25/10 |
| 2019/0094511 A1 | 3/2019 | Chan | |
| 2019/0114465 A1 * | 4/2019 | Shibata | C12M 41/00 |
| 2019/0180080 A1 * | 6/2019 | Iga | G06K 9/00134 |
| 2019/0376020 A1 | 12/2019 | Bickham et al. | |
| 2019/0376897 A1 | 12/2019 | Smith et al. | |
| 2020/0002661 A1 * | 1/2020 | Kesyou | C12M 31/00 |
| 2020/0064610 A1 * | 2/2020 | Echigo | C12M 1/00 |
| 2020/0082222 A1 | 3/2020 | Cohen et al. | |
| 2020/0217782 A1 * | 7/2020 | Fukushima | C12M 31/02 |
| 2020/0318058 A1 * | 10/2020 | Mochizuki | G01N 21/31 |
| 2020/0379231 A1 | 12/2020 | Dohi | |

FOREIGN PATENT DOCUMENTS

| | | |
|---|---|---|
| DE | 202009010255 U1 | 10/2009 |
| DE | 102016217250 A1 | 3/2018 |
| EP | 3009500 A1 | 4/2016 |
| EP | 3211469 A1 | 8/2017 |
| JP | 2013-516999 A | 5/2013 |
| JP | 2018-102228 A | 7/2018 |
| JP | 2018-125387 A | 8/2018 |
| WO | 2011090792 A1 | 7/2011 |
| WO | 2015/174356 A1 | 11/2015 |
| WO | 2016/158780 A1 | 10/2016 |
| WO | 2017/104068 A1 | 6/2017 |
| WO | 2018136797 A1 | 7/2018 |
| WO | 2018/207361 A1 | 11/2018 |

OTHER PUBLICATIONS

International Search Report and Written Opinion of the European International Searching Authority; PCT/US2019/063712; dated Feb. 27, 2020; 13 pgs.

Invitation to Pay Additional Fees and Partial Search Report of the European International Searching Authority; PCT/US2019/062137; dated Mar. 2, 2020; 17 pgs.

* cited by examiner

PRIOR ART

COMPACT OPTICAL IMAGING SYSTEM FOR CELL CULTURE MONITORING

CROSS-REFERENCE TO RELATED APPLICATION

This application claims the benefit of priority under 35 U.S.C § 120 of U.S. Provisional Application Ser. No. 62/773,899 filed on Nov. 30, 2018, the content of which is relied upon and incorporated herein by reference in its entirety

FIELD

The present disclosure generally relates to methods and devices for imaging of microscopic structures such as cells. More particularly, the present disclosure relates to systems and methods for cell culture imaging and monitoring.

BACKGROUND

Cell culture is an indispensable tool that has found many important and valuable applications in a wide range of areas such as drug screening, toxicity testing, genetic engineering, therapeutic protein and vaccine production. In general, mammalian cell lines are cultured in an incubator, where it is beneficial to closely monitor and control temperature, humidity and $CO_2$ content. During the cell culture processes, the cells seeded in a culture vessel filled with culture media must be monitored as they grow before being processed in downstream processes.

For example, people monitor the confluency of cell culture. As used herein, the term "confluency" is used to refer to the proportion of the cell culture substrate surface occupied by cells. Generally, cells are subcultured or passaged when they reach 80%-90% confluency because cells could lose their proliferating and gene expression phenotype when they become overgrown. In addition to cell confluency, a wide range of other important applications such as cell migration tracking, cell density measurement, and total cell number estimation also require frequent observation.

To visualize these applications, researchers usually use a bench top light microscope. Cell culture vessels containing both cells and cell culture media are taken out of cell incubator and placed on the specimen stage of a light microscope; through the ocular lens (eyepiece) of the microscope, researchers observe the cells in a bright field mode. However, the method of observation with a bench top light microscope has several major drawbacks. For example, researchers have to frequently manually take cell culture vessels out of the cell incubator. This procedure may interfere with the cell culture process because when the cell culture vessels are taken out of the cell incubator, the cells experience an environment change including temperature, atmosphere and humidity. Furthermore, there exists potential that cell culture gets contaminated due to frequent contact of cell culture vessels with incompletely sterilized labware outside of the cell incubator. The contamination of cell cultures with microorganisms (bacteria, fungi, yeast, etc.) can change the biochemical and biophysical behaviors of cells, or even cause the death of cells.

SUMMARY

According to an embodiment of the present disclosure, an optical monitoring system for cell culture monitoring is provided. The system includes an illumination system to emit light into a cell culture chamber, and an imaging system to image contents of the cell culture chamber that are illuminated by the illumination system. The illumination system and the imaging system are on disposed a same side of the cell culture chamber. The system is arranged to image contents of the cell culture chamber that are disposed on a first surface of the cell culture chamber. The optical monitoring system images the contents by redirecting the light emitted from the illumination system using a second surface of the cell culture vessel, the light being redirected toward the imaging system. The second surface is on an opposite side of the contents from the illumination system and the imaging system.

According to an embodiment of the present disclosure, a cell culture monitoring system for non-invasively monitoring a cell culture is provided. The system includes a cell culture vessel having a cell culture chamber with a surface on which cells are cultured. The system further includes at least one monitoring module having an optical monitoring system. The optical monitoring system includes an illumination system to emit light into a cell culture chamber, and an imaging system to image contents of the cell culture chamber that are illuminated by the illumination system. The illumination system and the imaging system are on disposed a same side of the cell culture chamber. The system is arranged to image contents of the cell culture chamber that are disposed on a first surface of the cell culture chamber. The optical monitoring system images the contents by redirecting the light emitted from the illumination system using a second surface of the cell culture vessel, the light being redirected toward the imaging system. The second surface is on an opposite side of the contents from the illumination system and the imaging system.

According to an embodiment of the present disclosure, an optical imaging system for cell culture monitoring is provided. The system includes an illumination source and a collimating lens positioned between a first surface of a cell culture vessel and the illumination source, wherein the illumination source is configured to emit light at an angle oblique to the first surface of the cell culture vessel, and a detector and a lens positioned between the first surface of the cell culture vessel and the detector, wherein the lens focuses light to the detector through an aperture stop, and wherein the detector is configured to receive light exiting the first surface of the cell culture vessel at an angle oblique to the first surface.

According to an embodiment of the present disclosure, a cell culture monitoring system configured to non-invasively measure a cell culture is provided. The system includes a plurality of cell culture layers, each of the plurality of cell culture layers comprising a cell culture chamber, the cell culture chamber having at least one surface to which cells adhere, at least one monitoring layer comprising an outer wall surrounding a monitoring layer cell culture chamber and having at least one surface to which cells adhere, the at least one monitoring layer comprising at least one indentation in the outer wall, and at least one monitoring module disposed in at least one of the at least one indentation and comprising at least one of an optical imaging system and an analyte monitor.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

The disclosure will be understood more clearly from the following description and from the accompanying figures, given purely by way of non-limiting example, in which.

DETAILED DESCRIPTION

Reference will now be made in detail to the present embodiment(s), an example(s) of which is/are illustrated in the accompanying drawings. Whenever possible, the same reference numerals will be used throughout the drawings to refer to the same or like parts.

The singular forms "a," "an" and "the" include plural referents unless the context clearly dictates otherwise. The endpoints of all ranges reciting the same characteristic are independently combinable and inclusive of the recited endpoint. All references are incorporated herein by reference.

As used herein, "have," "having," "include," "including," "comprise," "comprising" or the like are used in their open-ended sense, and generally mean "including, but not limited to."

All scientific and technical terms used herein have meanings commonly used in the art unless otherwise specified. The definitions provided herein are to facilitate understanding of certain terms used frequently herein and are not meant to limit the scope of the present disclosure.

The present disclosure is described below, at first generally, then in detail on the basis of several exemplary embodiments. The features shown in combination with one another in the individual exemplary embodiments do not all have to be realized. In particular, individual features may also be omitted or combined in some other way with other features shown of the same exemplary embodiment or else of other exemplary embodiments.

The terms "top", "bottom", "side", "upper", "lower", "above", "below" and the like are used herein for descriptive purposes and not necessarily for describing permanent relative positions. It should be understood that the terms so used are interchangeable under appropriate circumstances such that embodiments of the present disclosure are, for example, capable of operation in other orientations than those illustrated or otherwise described herein.

Figure 1:
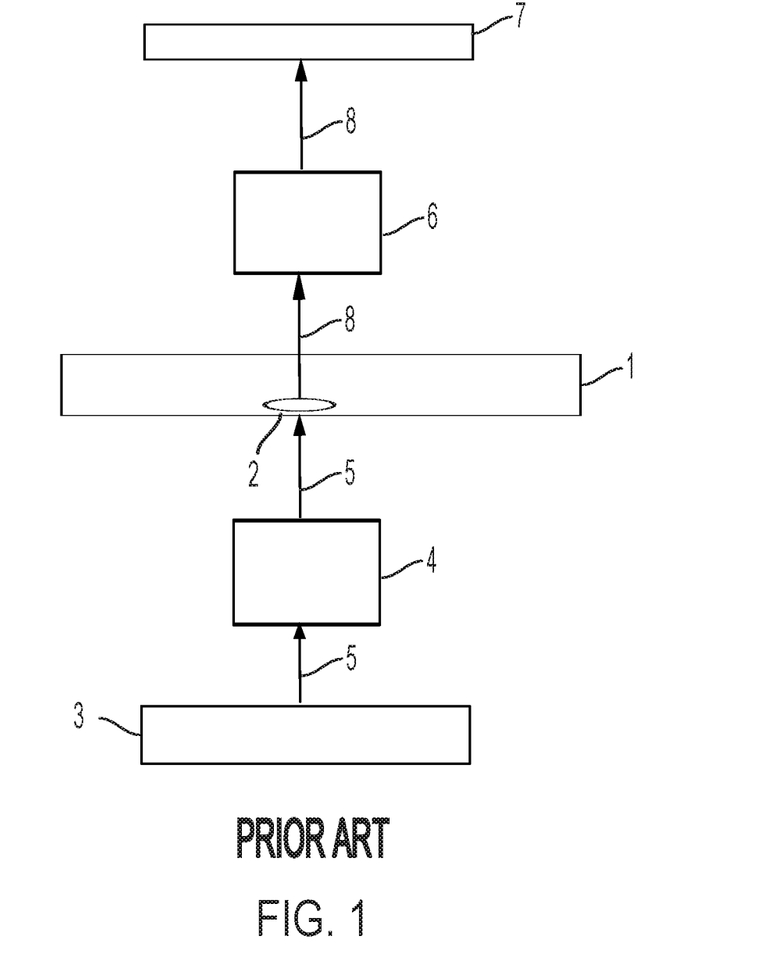
FIG. 1 schematically illustrates a conventional backlit microscope.

FIG. 1 illustrates an arrangement of components used in brightfield microscopy (or Koehler illumination). In Koehler illumination, the object of imaging is illuminated from behind. In other words, the object being imaging is between the source of illumination and the viewer of the image (or the detector detecting the image) of the object. For example, FIG. 1 shows a vessel 1 containing an object 2 (e.g., cells) to be imaged. A light source 3 projects light in an illumination path 5, which may pass through one or more optical components 4, such as one or more lenses. The light in the illumination path 5 then backlights the object 2. A backlight image is then projected along an imaging path 8 through an optical component 6 to a detector 7 (or viewer). The Koehler method is used because illumination required for viewing these cells with high contrast must come from behind the cells—that is, back illumination that transmits through the cells and then enters the objective lens of the microscope. However, this is challenging because the optical imaging system and the illumination system are located in different places (i.e., on opposite sides of the object or cells being imaged). This is especially problematic in real-world systems used for cell culture, where space is at a premium and vessels may be multi-layered cell culture vessels.

Embodiments of this disclosure provide the benefit of positioning the imaging and illumination channels on the same side of the cells being imaged. Thus, the imaging and illumination channels can be located in the same area of the cell culture stack to make modifications to the tray stacks and alignment between the channels easier. In addition, embodiments of this disclosure offer compact imaging solutions that allow cell culture vessels to remain in-place for imaging, eliminating the need to relocate a cell culture vessel to an imaging platform. Such relocation of the vessel is not desirable as it can disturb the cells and negatively impact the resulting cell culture.

Embodiments of the present disclosure relate to a compact optical imaging system for cell culture monitoring. The system includes an illumination source and a collimating lens, the collimating lens being positioned between a surface of a cell culture vessel and the illumination source, wherein the illumination source is configured to emit light at an angle oblique to the surface of the cell culture vessel, and a detector and a lens, the lens being positioned between the surface of the cell culture vessel and the detector, wherein the lens focuses light to the detector through an aperture stop, and wherein the detector is configured to receive light exiting the surface of the cell culture vessel at an angle oblique to the surface. The system is configured to be operated in bright field mode, which allows for various aspects of cell culture health to be determined through image analysis of a bright field image. Additionally, systems as described herein have a small footprint that permits the system to be integrated into, or removably associated with, a cell culture vessel in a way that allows for continuous monitoring of cell culture status using a bright field mode.

Figure 2:
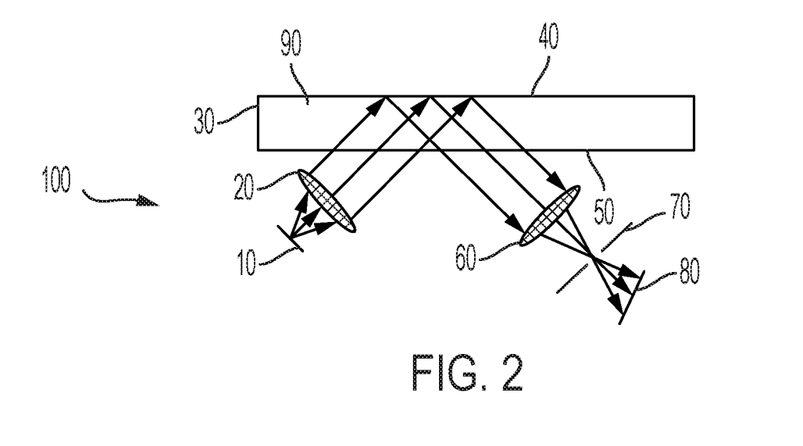
FIG. 2 schematically illustrates a compact optical imaging system for cell culture monitoring in accordance with embodiments of the present disclosure.

A compact optical imaging system for cell culture monitoring according to embodiments of the present disclosure is schematically illustrated in FIG. 2. It should be appreciated that the schematic illustration of FIG. 2 is not drawn to scale. As shown, the compact optical imaging system 100 includes an illumination source 10 and a collimating lens 20. The illumination source 10 is oriented to emit light that is collimated by the collimating lens 20 and directed toward a first surface 50 of a cell culture vessel 30. The illumination source 10 may be, for example but not limited to, a light emitting diode (LED), or an array of LEDs. Alternatively, the illumination source 10 may be a non-LED light source, such as an incandescent, compact fluorescent (CFL), halogen, or other source configured to produce and emit a beam of light. The illumination source 10 may produce a white light or a colored light of any wavelength or combination of wavelengths in the visible spectrum.

As further shown in FIG. 2, the compact optical imaging system 100 includes a detector 80. The detector 80 includes an image sensor for detecting light impinging on the sensor and converting the light into an electrical signal. Image sensor may be a charge-coupled device (CCD) sensor, a complementary metal oxide semiconductor (CMOS) sensor, or any other type of sensor that is capable of converting light into an electrical signal. Alternatively, the detector 80 may simply include a CCD, CMOS, or other sensor. The system 100 further includes a lens 60 for collecting light and an aperture stop 70 disposed between the first surface 50 of the cell culture vessel 30 and the detector 80, wherein the lens 60 collects light and focuses the light through the aperture stop 70 and onto the detector 80.

According to embodiments of the present disclosure, the illumination source 10, collimating lens 20, and any other optical components in the path of the light emitted from the illumination source 10 are positioned to transmit the light such that the direction of the light beam as it enters the cell culture vessel 100 is at an angle oblique to the first surface 50. Similarly, the detector 80 is positioned at an angle to receive light exiting the first surface 50 of the cell culture vessel 100 at an angle that is oblique to the surface 50. In operation of the compact optical imaging system 100, a light beam is emitted from the illumination source 10 in the direction of the first surface 50 of the cell culture vessel 30, wherein the first surface 50 contains live cells to be imaged. The light beam travels into and through a cell culture chamber 90 of the cell culture vessel 30, contacts a second surface 40 of the cell culture vessel 30 positioned on an opposite side of the cell culture chamber 90, and is redirected at an angle in the direction of the detector 80. After being redirected, the light passes through cells on the first surface 50 of the cell culture vessel 30 before being focused by lens 60 to the aperture stop 70 such that the source image size underfills the aperture size. The image of the illumination source 10 is created at the aperture stop 70 so that the source image underfills the aperture size. When underfilling the telecentric stop, the appropriate contrast is generated of the imaged cells so that they can be viewed clearly. The image of the illumination source is conjugate to the aperture stop.

As shown, the illumination source 10 and the detector 80 are configured to be positioned on the same side of the first surface 50 of the cell culture vessel 30. This configuration allows for the system 100 to operate in a bright field mode, thus backlighting the cells to be imaged. In a bright field mode, light from an illumination source enters an imaging objective lens assembly directly, and viewed objects absorb, change the phase of, or redirect some of the transmitted light such that the sample appears dark on a bright background. When operated in bright field mode, the system 100 allows for various aspects of cell culture health to be determined through image analysis of a bright field image, including, but not limited to, cell count, cell confluency, cell density, and cell migration tracking.

Figure 3:
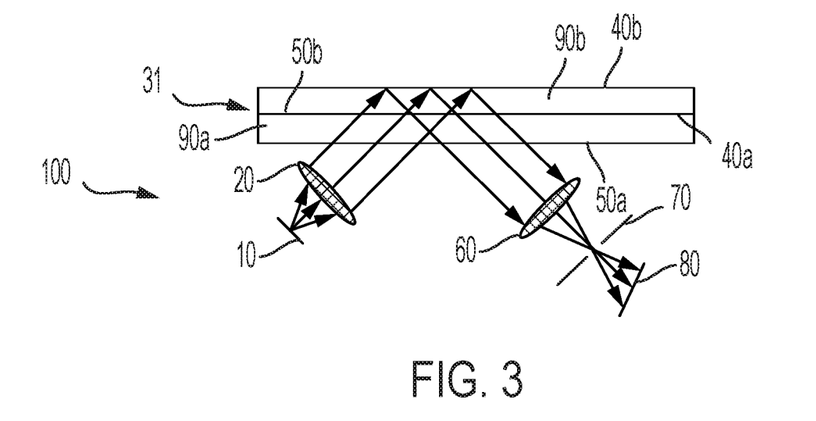
FIG. 3 schematically illustrates a compact optical imaging system for cell culture monitoring of a multilayer cell culture system in accordance with embodiments of the present disclosure.

FIG. 3 illustrates an example of the compact optical imaging system 100, according to embodiments of this disclosure, imaging cells in a multi-layered cell culture vessel 31. Components of the optical imaging system 100 correspond to those of like reference numerals in FIG. 2. The multi-layered cell culture vessel 31 includes a first cell culture chamber 90a having a first surface 50a and a second surface 40a on an opposite side of the first cell culture chamber 90a from the first surface 50a. The multi-layered cell culture vessel 31 further includes a second cell culture chamber 90b having a first surface 50b and a second surface 40b on an opposite side of the cell culture chamber 90b from the first surface 50b. The compact optical imaging system 100 operates similarly as described above with reference to FIG. 2. However, in the multi-layered cell culture vessel 31, the optical imaging system 100 can be arranged so that a light beam from the illumination source 10 can be redirected from a surface of the second cell culture chamber 90b toward the detection system.

According to embodiments of this disclosure, the cells to be imaged in a multi-layered cell culture vessel, such as the one shown in FIG. 3, for example, can be imaged using illumination that is redirected from a surface of a cell culture chamber other than the cell culture chamber containing the imaged cells. While the multi-layered cell culture vessel 31 of FIG. 3 only shows two cell culture chambers 90a, 90b, it is contemplated that embodiments of the compact optical imaging system can be used in multi-layered cell culture vessels having variety of numbers of layers or cell culture chambers. The light beam from the illumination source of the optical system can therefore be redirected by a surface of the cell culture chamber immediately above the cell culture chamber containing the cells to be imaged, or the light beam may be directed by a cell culture chamber that is two or more levels above the cell culture chamber containing the cells to be imaged. Further, the surface used to redirect the light beam from the illumination source can be a bottom surface (e.g., first surface 50b) of a cell culture chamber, or a top surface (e.g., second surface 40b) of a cell culture chamber. In some embodiments, as shown in FIGS. 2 and 3, for example, each cell culture chamber can have a top and bottom surface. It is contemplated that a top surface of a given cell culture chamber in a multi-layered cell culture vessel may be a bottom the above layer of the vessel.

Figure 4:
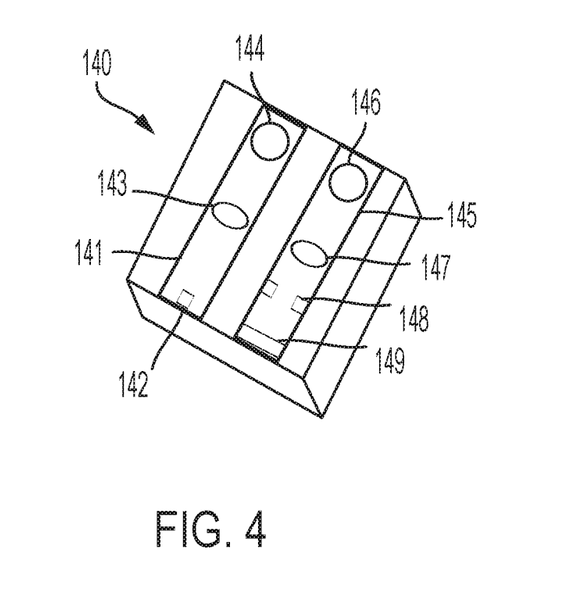
FIG. 4 illustrates an example of an imaging module in accordance with embodiments of the present disclosure.

FIG. 4 illustrates an imaging module 140 as an example of the imaging system 100, according to embodiments of the present disclosure. As described herein, the imaging module 140 may be sized and shaped to be positioned on or adjacent to a cell culture vessel for imaging cells contained in the vessel. In one example of an embodiment, the imaging module 140 is sized and shaped to fit within an indentation in the side of a monitoring layer of a vessel for non-invasively monitoring of the cell culture chamber. The imaging module 140 includes an illumination system 141 for backlighting cells in transmission, and an imaging system 145 for forming an image of an area of a surface of a cell culture vessel, as shown, for example, in FIGS. 2 and 3. The illumination system 141 includes an illumination source 142 and a lens 143, and the imaging system 145 includes a lens 147, an aperture stop 148, and a detector 149. As used herein, "lens" can refer to one or more optical elements directing and/or focusing light passing through the lens. The lens 143 of the illumination system 141 creates a collimated image of the light source such that the collimated image passes through a first surface (e.g., the cell growth surface) of a cell culture vessel and reflects off a second surface of the cell culture vessel to backlight cells growing on the first surface. The back illuminated light then enters the imaging system 145 and the image of the illumination source is re-imaged by the lens 147 into the aperture stop 148, and the image of the cells is then created on the detector 149. According to one or more embodiments, the aperture stop 148 is a telecentric stop. The telecentric stop is placed at the rear focal point of the lens 147 to ensure that the angular distribution of the light across the image is the same.

The illumination system 141 optionally includes a reflector 144 for redirecting the optical path of a light beam originating from the illumination source 142. Similarly, the imaging system 145 optionally includes a reflector 146 for redirecting the optical path of the light beam coming from the illumination source 142 via the cell culture chamber towards the lens 147 and/or detector 149. The use of reflectors 144, 146 can allow for the optical path to be controlled such that the imaging module 140 can be compact in size. For example, the illumination system 141 and the imaging system 145 may be substantially parallel to each other, and both the illumination system 141 and imaging system 145 can be substantially parallel to the surface of the cell culture chamber on which the cells are grown. This example arrangement allows for a compact imaging module 140 that can be integrated into a cell culture vessel, including a multi-layered cell culture vessel, without sacrificing much space. Due to the small size of the imaging module 140, a single cell culture vessel can accommodate multiple imaging modules 140 for monitoring multiple areas of the cell culture surface, or multiple layers within a multi-layered cell culture vessel. It should be appreciated that the imaging module 140 may be incorporated into a monitoring module that includes the imaging module 140 and an analyte monitor, as described below.

While the reflector 144 can be used to redirect the light from the illumination source, it should be understood that there are other ways to direct the light. For example, the illumination source 142 can be arranged within the imaging module 140 such that light from the illumination source is emitted directly into the cell culture vessel and the correct angle relative to the surface of the vessel. In some embodiment, the illumination source 142 can be offset from the axis of the illumination optic (e.g., lens 143). The amount of offset of the illumination source 142 will dictate the illumination angle of the light emitted from the illumination angle into the vessel.

Figure 5:
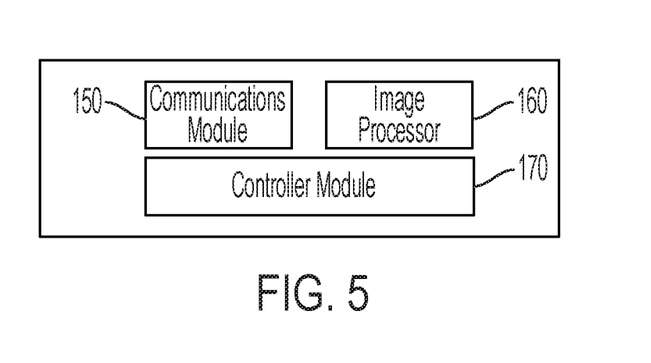
FIG. 5 schematically illustrates components of a compact optical imaging system for cell culture monitoring in accordance with embodiments of the present disclosure.

FIG. 5 further illustrates additional components of the compact optical imaging system 100. These components may be incorporated into the imaging module 140 of FIG. 4. As shown, the compact optical imaging system 100 may further include a controller module 170 configured to control the various components of the system 100. For example, the controller module 170 may be configured to control one or both of the illumination source 10 and/or the detector 80. The controller module 170 may also be configured to control one or both of the communications module 150 and the image processor 160.

The compact optical imaging system 100 may further include a communications module 150 configured to transfer images from the detector 80 to an image processor 160. The communication module 150 may be configured to communicate through a wired or wireless connection, including, but not limited to, a data connection conforming to one or more of the IEEE 802.11 family of standards (e.g., WiFi), a Bluetooth connection, a cellular network connection, an RF connection, a Universal Serial Bus (USB), an Ethernet connection, or any other data connection. The image processor 160 may be configured to record and analyze images received from the detector 80. The communications module 150, and image processor 160 may be on a single electronic device or multiple electronic devices, such as one or more desktop computers, laptop computers, tablet PCs, or other computer systems, as a user's particular setup of a compact optical imaging system 100 of the present disclosure may require. The controller module 170, communications module 150, and image processor 160 may interact so as to provide certain features to the compact optical imaging system 100. For example, the compact optical imaging system 100 may be adapted to record the cell culture image data (e.g., cell count, cell confluency, cell density, cell migration tracking, or bacterial contamination) in a non-transitory computer readable medium, and link the cell culture image data with the cell culture image from which the data was extracted. The compact optical imaging system 100 may be adapted to determine the cell culture health parameters over time through analysis of a time series of cell culture images. The compact optical imaging system 100 may provide additional functionality such as the ability to adjust the settings and parameters of the camera module, e.g., focal plane, aperture, shutter speed, sensitivity (e.g., ISO), white balance, etc. In some embodiments, the compact optical imaging system may be adapted to allow a user to record and/or analyze a cell culture image or video. In other embodiments, the compact optical imaging system 100 may allow a user to set a monitoring period and/or monitoring frequency, such that a cell culture image is recorded and/or analyzed once in a predefined time period for a predefined duration of time. In other embodiments, a cell culture image may be recorded and/or analyzed at a defined frequency continuously for an indefinite duration. In other embodiments, the compact optical imaging system 100 may communicate with a remote user device. The remote user device may be, e.g., a mobile phone device, a tablet computer, a desktop computer, a laptop computer or other computing system. The compact optical imaging system 100 may send one or more cell culture images and/or associated cell culture data to the remote user device. In some embodiments, the remote user device may be adapted to control the compact optical imaging system 100, including any of the functionality discussed above.

Figure 6:
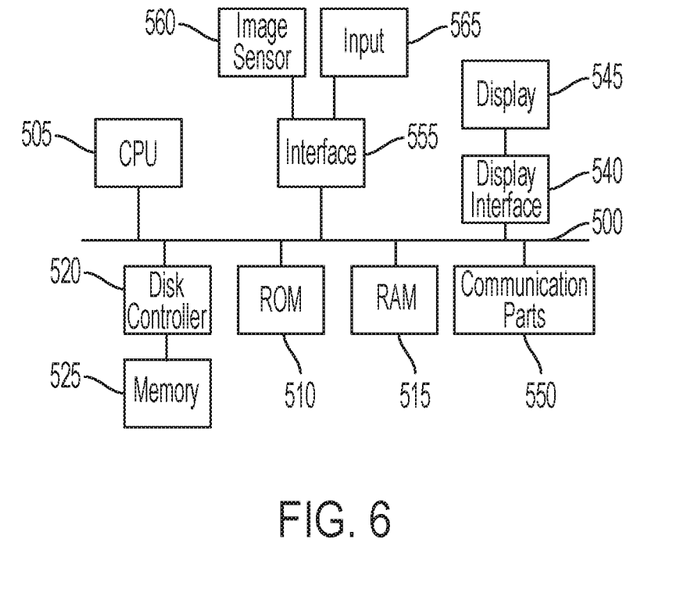
FIG. 6 depicts an example of internal hardware that may be used to implement the various computer processes and systems in accordance with embodiments of the present disclosure.

FIG. 6 depicts an example of internal hardware that may be used to contain or implement the various computer processes and systems as discussed herein. For example, the compact optical imaging system 100 or imaging module 140 discussed above may include mobile device hardware such as that illustrated in FIG. 6. An electrical bus 500 serves as an information highway interconnecting the other illustrated components of the hardware. CPU 505 is a central processing unit of the system, performing calculations and logic operations required to execute a program. CPU 505, alone or in conjunction with one or more of the other elements, is a processing device, computing device or processor as such terms are used within this disclosure. A CPU or "processor" is a component of an electronic device that executes programming instructions. The term "processor" may refer to either a single processor or to multiple processors that together implement various steps of a process. Unless the context specifically states that a single processor is required or that multiple processors are required, the term "processor" includes both the singular and plural embodiments. Read only memory (ROM) 510 and random access memory (RAM) 515 constitute examples of memory devices. The term "memory device" and similar terms include single device embodiments, multiple devices that together store programming or data, or individual sectors of such devices.

A controller 520 interfaces with one or more optional memory devices 525 that serves as data storage facilities to the system bus 500. These memory devices 525 may include, for example, an external or internal disk drive, a hard drive, flash memory, a USB drive or another type of device that serves as a data storage facility. As indicated previously, these various drives and controllers are optional devices. Additionally, the memory devices 525 may be configured to include individual files for storing any software modules or instructions, auxiliary data, incident data, common files for storing groups of contingency tables and/or regression models, or one or more databases for storing the information as discussed above.

Program instructions, software or interactive modules for performing any of the functional steps associated with the processes as described above may be stored in the ROM 510 and/or the RAM 515. Optionally, the program instructions may be stored on a non-transitory, computer readable medium such as a compact disk, a digital disk, flash memory, a memory card, a USB drive, an optical disc storage medium, and/or other recording medium.

An optional display interface 540 may permit information from the bus 500 to be displayed on the display 545 in audio, visual, graphic or alphanumeric format. Communication with external devices may occur using various communication ports 550. A communication port 550 may be attached to a communications network, such as the Internet, a local area network or a cellular telephone data network.

The hardware may also include an interface 555 which allows for receipt of data from input devices such as an imaging sensor 560 of a scanner or other input device 565 such as a keyboard, a mouse, a joystick, a touchscreen, a remote control, a pointing device, a video input device and/or an audio input device.

Accordingly, the system 100 or imaging module 140 may have a small footprint that permits the system 100 to be placed inside a normal incubator. As will be understood from the further description provided below, the small footprint of the system 100 as described herein permits the system 100 be integrated into a cell culture vessel 30, 31 or removably associated with a cell culture vessel 30, 31 in a way that allows for continuous monitoring of cell culture status using a bright field mode.

According to embodiments of the present disclosure, the compact optical imaging system 100 as described herein may be included as an integrated component, or a removable component, of a cell culture vessel 30, 31. The cell culture vessel 30, 31 may be any typical cell culture vessel including, but not limited to, a flask, dish, tube, multiple well plate, a microplate, a multilayer cell culture system, or a stacked cell culture vessel system. The cell culture vessel 100 may be made of a material transparent in the visible wavelength such as polystyrene, polycarbonate (PC), poly(methyl methacrylate) (PMMA), poly(ethylene terephthalate) (PET), or polypropylene (PP) or poly(dimethylsiloxane) (PDMS).

As described herein, a cell culture vessel 100 may include a monitoring layer including at least one indentation, the at least one indentation being configured to receive the compact optical imaging system 100 as described herein. Optionally, the at least one indentation, the at least one indentation may be configured to receive a monitoring module including the compact optical imaging system 100 as described herein. The cell culture vessels 30, 31 described herein may be adherent cell culture vessels generally including a planar surface on which cells adhere while being cultivated. Embodiments of the present disclosure enable the monitoring of cell confluence and a communication component may be utilized to transmit monitoring data from the compact optical imaging system 100 or the monitoring module to a user in a remote location. This configuration may be implemented in single use or multi-use stacked vessels.

In practice, cell culture systems that allow for certain measurements to be completed in real time without disturbing the cells, or in other words, a closed system, may facilitate maintaining a sterile cell growth environment. For example, a monitoring system that is external to a cell culture chamber may provide a non-invasive method for measuring cell status, such as cell growth and health, without directly contacting the cells and without contaminating the growth environment. As used herein, the term "closed system" refers to a system wherein the contents of the system are not open to the surrounding atmosphere. The system may include a closure apparatus, such as a cap, which limits or prevents the introduction of contaminants from the surrounding atmosphere. The system may be, but is not necessarily, sealed to ensure sterility of the contents of the system.

Embodiments of the present disclosure provide for closed-system operation of an adherent cell culture vessel with a monitoring module disposed external to cell culture layers. Embodiments of the present disclosure allow for the transmission of cell status from the monitoring layer to a user in a remote location. The monitoring layer may be positioned between other cell culture layers within a stacked cell culture vessel, and take measurements of cell culture chambers of the various layers of the stack. The closed system remains sterile and able to continuously grow cells, for example by remaining in an incubator, while taking real-time cell status data.

Positioning a compact optical imaging system 100 and/or a monitoring module external to a cell culture chamber may maintain sterility and enable remote and automated control of the process. By remotely monitoring cell confluence, embodiments of the present disclosure enable an operator to increase the yield in cell processing by optimizing the timing of next steps in cell production, thus reducing handling and reducing operating costs. This disclosure provides a mechanism to automate system controls allowing the operator to be a less skilled technician, lowering labor costs. With the external and remote implementation, the disclosure provides the main component to a closed cell production system that may be operated in a less costly environment.

Figure 7:
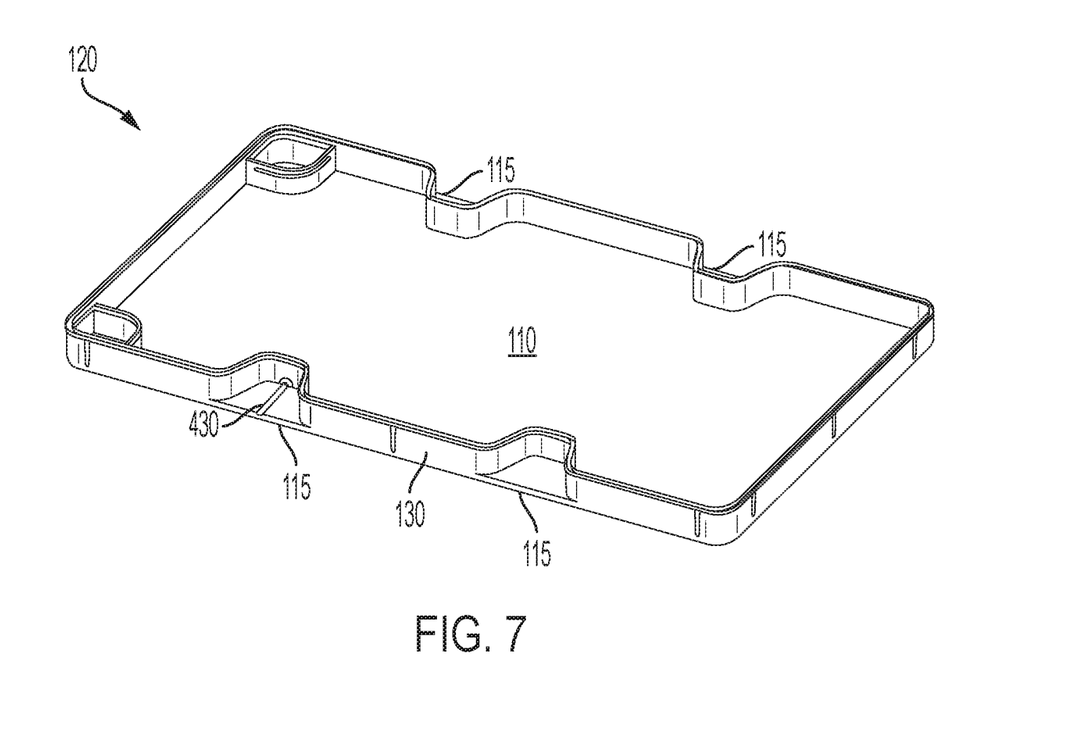
FIG. 7 illustrates a perspective view of an example of a monitoring layer for non-invasive measurement of a cell culture that supports remote monitoring in accordance with embodiments of the present disclosure.

FIG. 7 shows a perspective view of a monitoring layer for non-invasive measurement of cell culture chambers that supports cell culture monitoring in accordance with embodiments of the present disclosure. The monitoring layer 120 includes an outer wall 130 surrounding a cell culture chamber 110, and at least one indentation 115 extending inward from the outer wall 130 toward the interior of the cell culture chamber 110. While the monitoring layer 120 shown in FIG. 7 includes four indentations 115, it should be appreciated that monitoring layers 100 in accordance with embodiments of the present disclosure may include any number of indentations 115. As will be explained in more detail below, the indentations 115 are configured to receive an imaging module 140 or monitoring module 250. As such, the indentations 115 and the monitoring module 250 or imaging module 140 may have corresponding shapes. The monitoring layer 120 may be configured to operate in a wide temperature range, for example the monitoring layer 120 may operate in an incubator configured for cell growth. In some examples, the monitoring layer 120 may be part of a stacked cell culture vessel as shown in FIG. 9.

Figure 8:
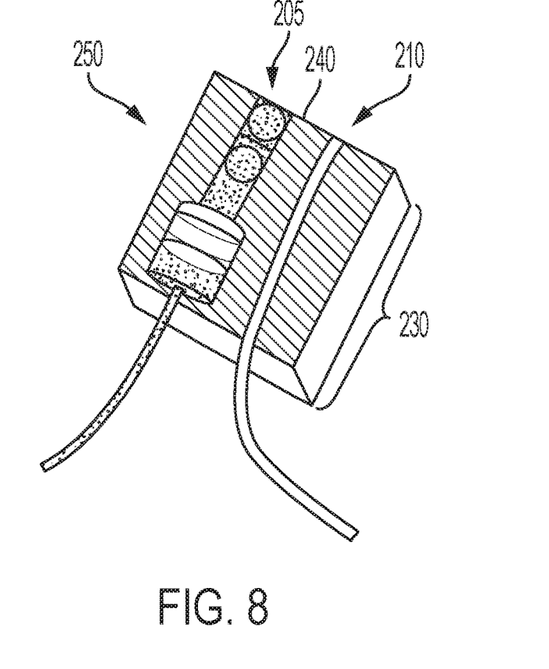
FIG. 8 illustrates an example of a monitoring module in accordance with embodiments of the present disclosure.

FIG. 8 illustrates a monitoring module in accordance with embodiments of the present disclosure. As described herein, the monitoring module 250 may include a head portion 230 having a front face 240 which is configured to contact an inner wall 410c of an indentation 115 of the monitoring layer 120 for non-invasively monitoring of the cell culture chamber. The monitoring module 250 further includes at least one of a compact optical imaging system 205 (having a configuration similar to the system 100 shown in FIG. 2 or the imaging module 140 of FIG. 4) and an analyte monitor 210. It should be appreciated that the monitoring module 250 may include one of a compact optical imaging system 205 and an analyte monitor 210 or, alternatively, as shown in FIG. 8, may include both of a compact optical imaging system 205 and an analyte monitor 210. The imaging module 140 of FIG. 4 is an example of a monitoring module with only an optical imaging system.

Figure 10:
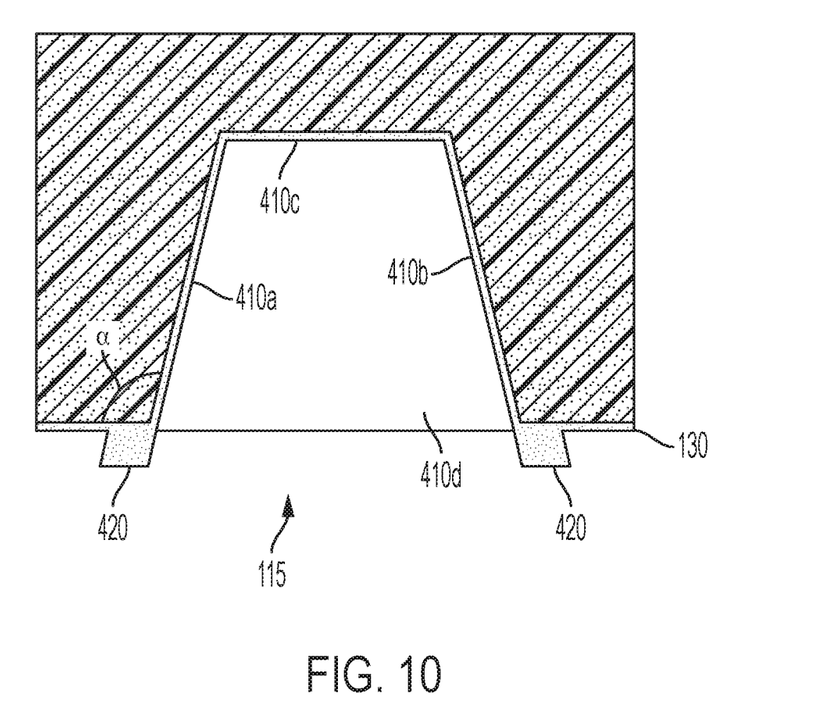
FIG. 10 illustrates an example of an indentation of a monitoring layer in accordance with embodiments of the present disclosure.

According to embodiments of the present disclosure, the monitoring module 250 (or imaging module 140) may have a shape corresponding to the shape of the indentation 115 of the monitoring layer 120 such that the module 140, 250 may be received into the indentation 115. As shown in FIG. 10, the indentation 115 may have sidewalls 410a and 410b and an inner wall 410c. The sidewalls 410a, 410b may extend from the outer wall 130 of the monitoring layer 120 to the inner wall 410c of the indentation 115 at an angle α that is greater than about 90 degrees such that the indentation 115 has an isosceles trapezoid shape. For example, the head portion 230 of the monitoring module 250 may have a corresponding isosceles trapezoid shape, or may have an orthogonal shape where the front face 240 of the head portion 230 has a width that is no greater than the width of the inner wall 410c of the indentation 115. Alternatively, the sidewalls 410a, 410b may extend perpendicular to the outer wall 130 of the monitoring layer 120 and parallel to each other. As such, the head portion 230 of the monitoring module 250, such as is illustrated in FIG. 8, may have an orthogonal shape which corresponds to the shape formed by the sidewalls 410a, 410b extending perpendicular to the outer wall 130. Alternatively, the sidewalls 410a, 410b may have a concave shape and the head portion 230 of the monitoring module 250 may have a rounded features configured to be received in the concave-shaped sidewalls 410a, 410b of the indentation 115. The shapes of the indentations 115 of the monitoring layer 120 and the head portion 230 of the monitoring module 250 discussed above are meant merely as examples. The indentations 115 may have any shape and the monitoring module 250 may have any corresponding shape such that the monitoring module 250 may be received in the indentation 115 and that the front face 240 of the head portion 230 contacts the inner wall 410c of the indentation 115.

Figure 9:
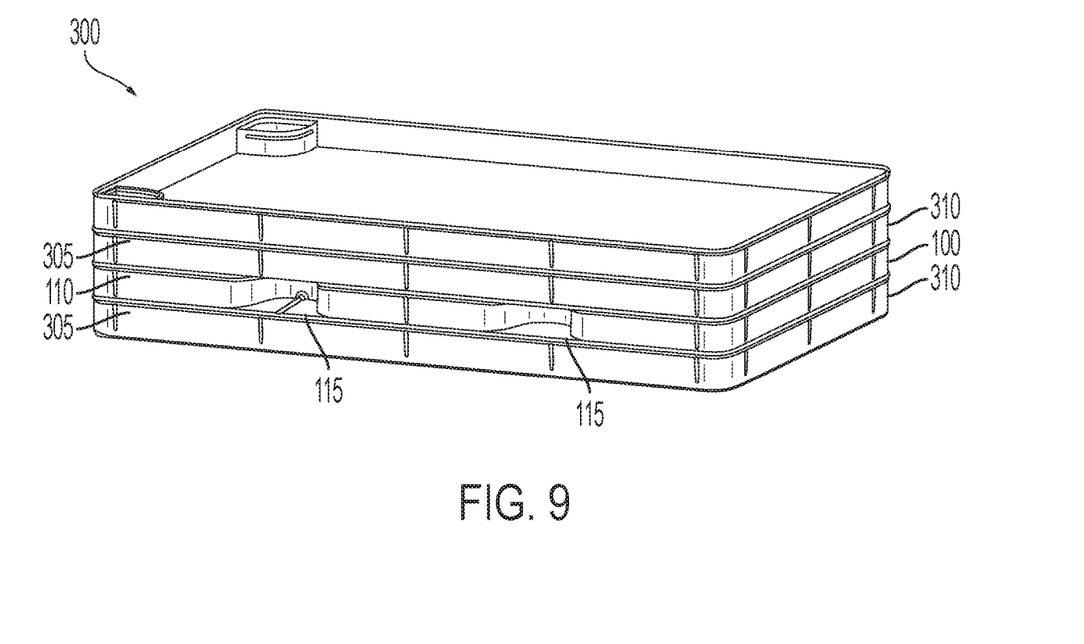
FIG. 9 illustrates a perspective view of an example of a stacked cell culture vessel system for non-invasive measurement of a cell culture that supports remote monitoring in accordance with embodiments of the present disclosure.

FIG. 9 shows a perspective view of a stacked cell culture vessel system 300 that can be used, in conjunction with a monitoring module 250, for non-invasive measurement of a cell culture chamber 110, 305 in accordance with embodiments of the present disclosure. The stacked cell culture vessel system 300 may include a plurality of cell culture layers 310 and at least one monitoring layer 120.

As illustrated, the stacked cell culture vessel system 300 may include any number of cell culture layers 310 and any number of monitoring layers 120. As shown in FIG. 9, the cell culture vessel system 300 may include a cell culture layer 310 below a monitoring layer 120 and a cell culture layer 310 above the monitoring layer 120. Where the cell culture vessel system 300 includes a plurality of monitoring layers 100, the system 300 may include any number of cell culture layers 310 between any two of the plurality of monitoring layers 120. For example, the cell culture vessel system 300 may include between 1 and 50 cell culture layers 310 between each monitoring layer 120, such as between or 2 and 40 cell culture layers 310, or between 3 and 35 cell culture layers 310, or between 5 and 30 cell culture layers 310, or even between 10 and 25 cell culture layers 310 between each monitoring layer 120, and all values therebetween. It should be appreciated that the number of cell culture layers 310 between different sets of the plurality of monitoring layers 100 may vary within the same stacked cell culture vessel system 300. Additionally, the stacked cell culture vessel system 300 may be configured to operate over a wide temperature range such as in an incubator at a temperature designed for cell growth.

FIG. 10 further illustrates exemplary retaining features in accordance with embodiments of the present disclosure. As shown, the outer wall 130 of the monitoring layer 120 includes clips 420 at the edges of the opening formed by the sidewalls 410a and 410b of the indentation 115. The clips 420 are configured to fit into a corresponding receptor on the monitoring module 250, thus maintaining the monitoring module 250 within the indentation 115. Another exemplary retaining feature is shown in FIG. 7. As shown, a base portion 410d of the indentation 115 includes a raised channel 430. The raised channel 430 is configured to fit into a corresponding notch on the bottom of the monitoring module 250, thus maintaining the monitoring module 250 within the indentation 115. As another option, the retaining feature may be a biased retention clip (not shown) on at least one surface of the monitoring module 250. The biased retention clip may have a similar design and function as those known to be used for telephone line connectors and Ethernet cable connectors. The indentations may include at least one clip groove (not shown) which receives a corresponding biased retention clip on a surface of the monitoring module 250 and which, in conjunction with the biased retention clip, limits motion of the monitoring module 250 and maintains the monitoring module 250 within the indentation 115.

According to embodiments of the present disclosure, the compact optical imaging system 250 and the analyte monitors 215 may capture the cell status of the cells and analyte status of the media in cell culture chambers 110, 305, including inter-layer measurements and monitoring. In some cases, a single compact optical imaging system 100 may monitor cell status of the cells of multiple stacked cell culture chambers 110, 305, or a single analyte monitor 215 may monitor analyte status of the media of multiple stacked cell culture chambers 110, 305.

The compact optical imaging system 205 may be configured to measure cell status in the cell culture chamber 110 of the monitoring layer 120, or may be configured to measure cell status in a cell culture chamber 305 of a cell culture layer 310 positioned above or below the monitoring layer 120. Similarly, the analyte monitor 210 may be configured to monitor analytes in the cell culture chamber 110 of the monitoring layer 120, or may be configured to monitor analytes in a cell culture chamber 305 of a cell culture layer 310 positioned above or below the monitoring layer 120. Where the monitoring module 250 includes both a compact optical imaging system 205 and an analyte monitor 210, both the system 205 and the monitor 210 may be configured to monitor the cell culture chamber 110 of the monitoring layer 120, or both the system 205 and the monitor 210 may be configured to monitor at least one cell culture chamber 305 of a cell culture layer 310 positioned above or below the monitoring layer 120. Optionally, where the monitoring module 250 includes both a compact optical imaging system 205 and an analyte monitor 210, one of the compact optical imaging system 205 and the analyte monitor 210 may be configured to monitor the cell culture chamber 110 of the monitoring layer 120 and the other of the compact optical imaging system 205 and the analyte monitor 210 may be configured to monitor at least one cell culture chamber 305 of a cell culture layer 310 positioned above or below the monitoring layer 120.

As one non-limiting example, the illumination system 141 or the compact optical imaging system 205 may be configured as described in FIG. 2 or FIG. 3 such that the direction of the light beam emitted by the illumination source enters a cell culture chamber 305 of a cell culture layer 310 positioned above or below the monitoring layer 120 at an angle oblique to the surface of the cell culture layer 310. Similarly, the detector 149 of the imaging system 145 or the detector of the system 205 is positioned at an oblique angle relative to the direction of the light beam being received by the detector from the cell culture layer 310 positioned above or below the monitoring layer 120. The direction of the light beam is also at an angle that is oblique to the surface of the cell culture layer 310 as it passes through the area of the cell culture layer 310 where the cells being imaged are located. Because the light passes through the surface of the cell culture vessel at an oblique angle, the light beam is also at an oblique angle relative to the cells adhered to that surface. This will result in a focus shift across the field of view if the detector is perpendicular to the light beam. Thus, the detector can be positioned at an oblique angle relative to the light beam so that the cells can be imaging in focus across the field of view, in accordance with the Scheimpflug principle. In operation of the compact optical imaging system 205, a light beam is emitted from the illumination source positioned in the monitoring layer 120 in the direction of the cell culture layer 310 positioned above or below the monitoring layer 120, wherein a first surface of the cell culture layer 310 contains live cells to be imaged. The light beam travels into and through the cell culture chamber 305 of the cell culture layer 310, contacts a second surface of the cell culture layer 310 positioned on an opposite side of the cell culture chamber 305, and is redirected at an angle in the direction of the detector positioned in the monitoring layer 120. After being redirected, the light passes through cells on the first surface of the cell culture layer 310 and is focused to the detector positioned in the monitoring layer 120.

Illustrative Implementations

The following is a description of various aspects of implementations of the disclosed subject matter. Each aspect may include one or more of the various features, characteristics, or advantages of the disclosed subject matter. The implementations are intended to illustrate a few aspects of the disclosed subject matter and should not be considered a comprehensive or exhaustive description of all possible implementations.

Aspect 1 is directed to an optical monitoring system for cell culture monitoring comprising: an illumination system configured to emit light into a cell culture chamber; and an imaging system configured to image contents of the cell culture chamber that are illuminated by the illumination system, wherein the illumination system and the imaging system are on a same side of the cell culture chamber.

Aspect 2 is directed to the optical monitoring system of Aspect 1, wherein the contents are disposed on a first surface of the cell culture chamber.

Aspect 3 is directed to the optical monitoring system of Aspect 1 or Aspect 2, wherein the optical monitoring system is configured to image the contents by redirecting the light emitted from the illumination system using a second surface of the cell culture vessel, the light being redirected toward the imaging system, wherein the second surface is on an opposite side of the contents from the illumination system and the imaging system.

Aspect 4 is directed to the optical monitoring system of any of Aspects 1-3, wherein the illumination system comprises: an illumination source configured to emit the light; and a collimating lens arranged in an optical path of the light between the illumination source and the contents.

Aspect 4 is directed to the optical monitoring system of any of Aspects 1-4, wherein the illumination system further comprises a mirror for redirecting the light from the illumination system toward the cell culture chamber.

Aspect 5 is directed to the optical monitoring system of any of Aspects 1-3, wherein the imaging system comprises: a detector for receiving an image of the contents; and an imaging lens positioned in an optical path of the light between the contents and the detector.

Aspect 6 is directed to the optical monitoring system of Aspect 5, wherein the imaging system further comprises an aperture stop disposed in an optical path of the light between the imaging lens and the detector.

Aspect 7 is directed to the optical monitoring system of Aspect 6, wherein the aperture stop is a telecentric stop.

Aspect 8 is directed to the optical monitoring system of any of Aspects 2-7, wherein the light emitted from the illumination system is transmitted through the first surface at an oblique angle to the first surface.

Aspect 9 is directed to the optical monitoring system of any of Aspects 2-8, wherein the light redirected toward the imaging system is transmitted through the first surface at an oblique angle to the first surface.

Aspect 10 is directed to the optical monitoring system of any of Aspects 1-9, wherein the detector comprises a detection surface, wherein a normal line to the detection surface is at an oblique angle relative to an optical path direction of the light incident on the detection surface.

Aspect 11 is directed to the optical monitoring system of Aspect 10, wherein the oblique angle of the normal line of the detection surface relative to the optical path direction is configured to produce an image of the contents that is in focus across a field of view of the image.

Aspect 12 is directed to the optical monitoring system of any of Aspects 2-12, wherein the first surface is a bottom surface of a first cell culture chamber of the cell culture vessel, the bottom surface being configured to culture cells thereon, and wherein the second surface is at least one of a top surface of the first cell culture chamber, a bottom surface of a second cell culture chamber of the cell culture vessel, a top surface of the second cell culture chamber, and another surface of the cell culture vessel, and wherein the second cell culture chamber is disposed on an opposite side of the first cell culture chamber from the illumination system and the imaging system.

Aspect 13 is directed to the optical monitoring system of any of Aspects 1-12, wherein the cell culture vessel comprises a plurality of cell culture chambers.

Aspect 14 is directed to the optical monitoring system of any of Aspects 3-13, wherein the illumination source offset from an optical axis of the collimating lens.

Aspect 15 is directed to the optical monitoring system of any of Aspects 3-14, wherein the illumination source comprises at least one of a light emitting diode (LED) or a non-LED source.

Aspect 16 is directed to the optical monitoring system of any of Aspects 5-15, wherein the detector comprises a sensor configured to convert light into an electrical signal.

Aspect 17 is directed to the optical monitoring system of Aspect 16, wherein the detector comprises a sensor selected from the group consisting of a charge-coupled device (CCD) sensor, and a complementary metal oxide semiconductor (CMOS) sensor.

Aspect 18 is directed to the optical monitoring system of any of Aspects 1-17, further comprising a controller module configured to control the system.

Aspect 19 is directed to the optical monitoring system of any of Aspects 1-18, further comprising a communications module configured to transfer images from the imaging system or the detector to an image processor.

Aspect 20 is directed to the optical monitoring system of Aspect 19, wherein the communications module is configured to communicate through at least one of a wired connection and a wireless connection.

Aspect 21 is directed to a cell culture monitoring system configured to non-invasively monitor a cell culture, the system comprising: a cell culture vessel comprising a cell culture chamber, the cell culture chamber having a surface on which cells are cultured; and at least one monitoring module comprising the optical monitoring system of any of Aspects 1-20.

Aspect 22 is directed to the cell culture monitoring system of Aspect 21, wherein the cell culture vessel comprises a plurality of cell culture chambers in a stacked arrangement.

Aspect 23 is directed to the cell culture monitoring system of Aspect 21 or Aspect 22, further comprising at least one monitoring layer in a stacked arrangement with the cell culture chamber, the at least one monitoring module being disposed in the at least one monitoring layer.

Aspect 24 is directed to the cell culture monitoring system of Aspect 23, wherein the at least one monitoring layer comprises an outer wall surrounding a monitoring layer cell culture chamber and having at least one surface to which cells adhere, the at least one monitoring layer comprising at least one indentation in the outer wall, and wherein the at least one monitoring module is disposed in at least one of the at least one indentation.

Aspect 25 is directed to the cell culture monitoring system of any of Aspects 21-24, wherein the monitoring module further comprises an analyte monitor configured monitor an analyte in the cell culture chamber.

Aspect 26 is directed to the cell culture monitoring system of any of Aspects 23-25, wherein monitoring module is configured monitor a cell culture chamber of a cell culture layer positioned above or below the at least one monitoring layer.

Aspect 27 is directed to an optical imaging system for cell culture monitoring comprising: an illumination segment comprising an illumination source and a collimating lens positioned between a first surface of a cell culture vessel and the illumination source, wherein the illumination source and the collimating lens are configured to transmit light from the illumination source through the first surface at an angle oblique to the first surface of the cell culture vessel; a detection segment comprising a detector and a lens positioned between the first surface of the cell culture vessel and the detector, wherein the lens focuses light to the detector through an aperture stop, and wherein the detector is configured to receive light exiting the first surface of the cell culture vessel, the light exiting the first surface at an angle oblique to the first surface.

Aspect 28 is directed to the optical imaging system of Aspect 27, wherein the illumination segment and the detection segment are configured so that light emitted from the illumination segment contacts a second surface of the cell culture vessel positioned, relative to the first surface, on an opposite side of a cell culture chamber of the cell culture vessel, and is redirected by the second surface toward the detection segment.

Aspect 29 is directed to the optical imaging system of Aspect 28, wherein the light is transmitted by the illumination segment through the first surface toward the second surface at an oblique angle to the first surface, and wherein the light from the second surface is transmitted through the first surface toward the detection segment at an oblique angle to the first surface.

Aspect 30 is directed to the optical imaging system of any of Aspects 27-29, wherein the illumination source comprises a light emitting diode.

Aspect 31 is directed to the optical imaging system of any one of Aspects 27-30, wherein the illumination source comprises a non-light emitting diode source.

Aspect 32 is directed to the optical imaging system of Aspect 27, wherein the detector comprises a sensor configured to convert light into an electrical signal.

Aspect 33 is directed to the optical imaging system of Aspect 27, wherein the detector comprises a sensor selected from the group consisting of a charge-coupled device (CCD) sensor, and a complementary metal oxide semiconductor (CMOS) sensor.

Aspect 34 is directed to the optical imaging system of any of Aspects 27-33 further comprising a controller module configured to control the system.

Aspect 35 is directed to the optical imaging system of any of Aspects 27-34 further comprising a communications module configured to transfer images from the detector to an image processor.

Aspect 36 is directed to the optical imaging system of Aspect 35, wherein the communications module is configured to communicate through a wired connection.

Aspect 37 is directed to the optical imaging system of Aspect 35, wherein the communications module is configured to communicate through a wireless connection.

Aspect 38 is directed to a cell culture monitoring system configured to non-invasively measure a cell culture, the system comprising: a plurality of cell culture layers, each of the plurality of cell culture layers comprising a cell culture chamber, the cell culture chamber having at least one surface to which cells adhere; at least one monitoring layer comprising an outer wall surrounding a monitoring layer cell culture chamber and having at least one surface to which cells adhere, the at least one monitoring layer comprising at least one indentation in the outer wall; and at least one monitoring module disposed in at least one of the at least one indentation and comprising at least one of an optical imaging system and an analyte monitor.

Aspect 39 is directed to the system of Aspect 38, wherein the at least one monitoring module comprises both an optical imaging system and an analyte monitor.

Aspect 40 is directed to the system of Aspect 38, wherein at least one of the optical imaging system and the analyte monitor is configured monitor a cell culture chamber of a cell culture layer positioned above or below the at least one monitoring layer.

Aspect 41 is directed to the system of Aspect 38, wherein the at least one indentation comprises an inner wall configured to contact a front face of a head portion of the at least one monitoring module.

Aspect 42 is directed to the system of Aspect 38, comprising a plurality of monitoring layers.

Aspect 43 is directed to the system of Aspect 42, comprising between 1 and 50 cell culture layers between two of the plurality of monitoring layers.

Aspect 44 is directed to the system of Aspect 42, comprising between 2 and 40 cell culture layers between two of the plurality of monitoring layers.

Aspect 45 is directed to the system of Aspect 42, comprising between 3 and 35 cell culture layers between two of the plurality of monitoring layers.

Aspect 46 is directed to the system of Aspect 42, comprising between 5 and 30 cell culture layers between two of the plurality of monitoring layers.

Aspect 47 is directed to the system of Aspect 42, comprising between 10 and 25 cell culture layers between two of the plurality of monitoring layers.

Aspect 48 is directed to the system of Aspect 38, wherein the optical imaging system comprises: an illumination segment comprising an illumination source and a collimating lens positioned between a first surface of at least one of the plurality of cell culture layers and the illumination source, wherein the illumination source and the collimating lens are configured to transmit light from the illumination source through the first surface at an angle oblique to the first surface of the cell culture layer; and a detection segment comprising a detector and a lens positioned between the first surface of the cell culture layer and the detector, wherein the lens focuses light to the detector through an aperture stop, and wherein the detector is configured to receive light exiting the first surface of the cell culture layer, the light exiting the first surface at an angle oblique to the first surface.

Aspect 49 is directed to the system of Aspect 48, wherein light emitted from the illumination source contacts a second surface of the cell culture vessel positioned, relative to the first surface, on an opposite side of a cell culture chamber of the cell culture vessel, and is redirected by the second surface toward the detection segment.

Aspect 50 is directed to the system of any of Aspects 48-49, wherein the illumination source comprises a light emitting diode.

Aspect 51 is directed to the system of any of Aspects 48-49, wherein the illumination source comprises a non-light emitting diode source.

Aspect 52 is directed to the system of any of Aspects 48-51, wherein the detector comprises a sensor configured to convert light into an electrical signal.

Aspect 53 is directed to the system of any of Aspects 48-52, further comprising a communications module configured to transfer images from the detector to an image processor.

Aspect 54 is directed to the system of Aspect 53, wherein the communications module is configured to communicate through a wired connection.

Aspect 55 is directed to the system of Aspect 53, wherein the communications module is configured to communicate through a wireless connection.

While the present disclosure includes a limited number of embodiments, those skilled in the art, having benefit of this disclosure, will appreciate that other embodiments can be devised which do not depart from the scope of the present disclosure.

What is claimed is:

1. A cell culture monitoring system configured to non-invasively monitor a cell culture, the system comprising:
a cell culture vessel comprising a plurality of cell culture chambers in a stacked arrangement, each of the plurality of cell culture chambers having a surface on which cells are cultured;
at least one monitoring layer in the stacked arrangement of the plurality of cell culture chambers, the at least one monitoring layer comprising an outer wall surrounding a monitoring layer cell culture chamber within the stacked arrangement of the plurality of cell culture chambers and having at least one surface to which cells adhere, the at least one monitoring layer comprising at least one indentation in the outer wall; and
at least one monitoring module disposed in the at least one indentation in the outer wall, the monitoring module comprising:
an illumination system configured to emit light into at least one of the cell culture chambers;
an imaging system configured to image contents of the at least one cell culture chamber that are illuminated by the illumination system,
wherein the illumination system and the imaging system are on a same side of the monitoring module;
wherein the at least one monitoring module is configured to monitor a cell culture chamber of a cell culture layer positioned both above and below the at least one monitoring layer, and wherein the at least one indentation in the outer wall is on a sidewall of the outer wall.

2. The cell culture monitoring system of claim 1, wherein the monitoring module further comprises an analyte monitor configured monitor an analyte in the cell culture chamber.

3. The cell culture monitoring system of claim 1, wherein the contents are disposed on a first surface of the cell culture chamber.

4. The cell culture monitoring system of claim 1, wherein the optical monitoring system is configured to image the contents by redirecting the light emitted from the illumination system using a second surface of the cell culture vessel, the light being redirected toward the imaging system,
wherein the second surface is on an opposite side of the contents from the illumination system and the imaging system.

5. The cell culture monitoring system of claim 1, wherein the illumination system comprises:
an illumination source configured to emit the light; and
a collimating lens arranged in an optical path of the light between the illumination source and the contents.

6. The cell culture monitoring system of claim 5, wherein the illumination system further comprises a mirror for redirecting the light from the illumination system toward the cell culture chamber.

7. The cell culture monitoring system of claim 1, wherein the imaging system comprises:

a detector for receiving an image of the contents; and
an imaging lens positioned in an optical path of the light between the contents and the detector.

8. The cell culture monitoring system of claim 7, wherein the imaging system further comprises an aperture stop disposed in an optical path of the light between the imaging lens and the detector.

9. The cell culture monitoring system of claim 8, wherein the aperture stop is a telecentric stop.

10. The cell culture monitoring system of claim 3, wherein the light emitted from the illumination system is transmitted through the first surface at an oblique angle to the first surface.

11. The cell culture monitoring system of claim 3, wherein the light redirected toward the imaging system is transmitted through the first surface at an oblique angle to the first surface.

12. The cell culture monitoring system of claim 7, wherein the detector comprises a detection surface, wherein a normal line to the detection surface is at an oblique angle relative to an optical path direction of the light incident on the detection surface.

13. The cell culture monitoring system of claim 12, wherein the oblique angle of the normal line of the detection surface relative to the optical path direction is configured to produce an image of the contents that is in focus across a field of view of the image.

14. The cell culture monitoring system of claim 4, wherein the first surface is a bottom surface of a first cell culture chamber of the cell culture vessel, the bottom surface being configured to culture cells thereon, and
wherein the second surface is at least one of a top surface of the first cell culture chamber, a bottom surface of a second cell culture chamber of the cell culture vessel, a top surface of the second cell culture chamber, and another surface of the cell culture vessel, and
wherein the second cell culture chamber is disposed on an opposite side of the first cell culture chamber from the illumination system and the imaging system.

15. The cell culture monitoring system of claim 1, wherein the cell culture vessel comprises a plurality of cell culture chambers.

16. The cell culture monitoring system of claim 5, wherein the illumination source offset from an optical axis of the collimating lens.

17. The cell culture monitoring system of claim 5, wherein the illumination source comprises a light emitting diode (LED) source.

18. The cell culture monitoring system of claim 7, wherein the detector comprises a sensor configured to convert light into an electrical signal.

19. The cell culture monitoring system of claim 18, wherein the detector comprises a sensor selected from the group consisting of a charge-coupled device (CCD) sensor, and a complementary metal oxide semiconductor (CMOS) sensor.

20. The cell culture monitoring system of claim 1, further comprising a controller module configured to control the system.

21. The cell culture monitoring system of claim 1, further comprising a communications module configured to transfer images from the imaging system to an image processor through at least one of a wired connection and a wireless connection.

* * * * *